United States Patent
Seidelbach

(10) Patent No.: US 6,441,257 B1
(45) Date of Patent: Aug. 27, 2002

(54) PROCESS FOR THE TREATMENT OF A CRACKING GAS FROM THE CRACKING OF 1,2-DICHLOROETHANE

(75) Inventor: Friedrich Seidelbach, Wiesbaden (DE)

(73) Assignee: Krupp Uhde GmbH, Dortmund (DE)

( * ) Notice: Subject to any disclaimer, the term of this patent is extended or adjusted under 35 U.S.C. 154(b) by 0 days.

(21) Appl. No.: 09/685,107

(22) Filed: Oct. 9, 2000

(51) Int. Cl.⁷ ............................ C07C 17/38; C07C 17/25
(52) U.S. Cl. ........................................ 570/238; 570/226
(58) Field of Search ................................ 570/226, 238

(56) References Cited

U.S. PATENT DOCUMENTS

| | | |
|---|---|---|
| 3,468,967 A | 9/1969 | Wall et al. |
| 3,655,787 A | 4/1972 | Wiley |
| 4,822,932 A | 4/1989 | Dummer et al. |
| 5,507,921 A | 4/1996 | Best |

FOREIGN PATENT DOCUMENTS

DE          4132761 A1     4/1993

Primary Examiner—Alan Siegel
(74) Attorney, Agent, or Firm—Katten Muchin Zavis Rosenman

(57) ABSTRACT

In a process for the treatment of a cracking gas formed by pyrolysis of 1,2-dichloroethane (EDC), in which the cracking gas is split into its principal components hydrogen chloride (HCl), vinyl chloride (VCM) and unreacted 1,2-dichloroethane (EDC), and these are formed in substantially pure form, where, in the first step of the treatment of the cracking gas, the solids are separated therefrom in a quench zone, the disadvantages of the prior art are intended to be reduced at least partly and in particular the energy losses which usually arise due to the substantial condensation of the quench gas and its re-heating for the purposes of distillative separation are avoided and, due to the circulation of the unreacted EDC at a higher temperature level, the original conversion in the pyrolytic cracking of EDC is intended to be subsequently increased.

Figure 1:
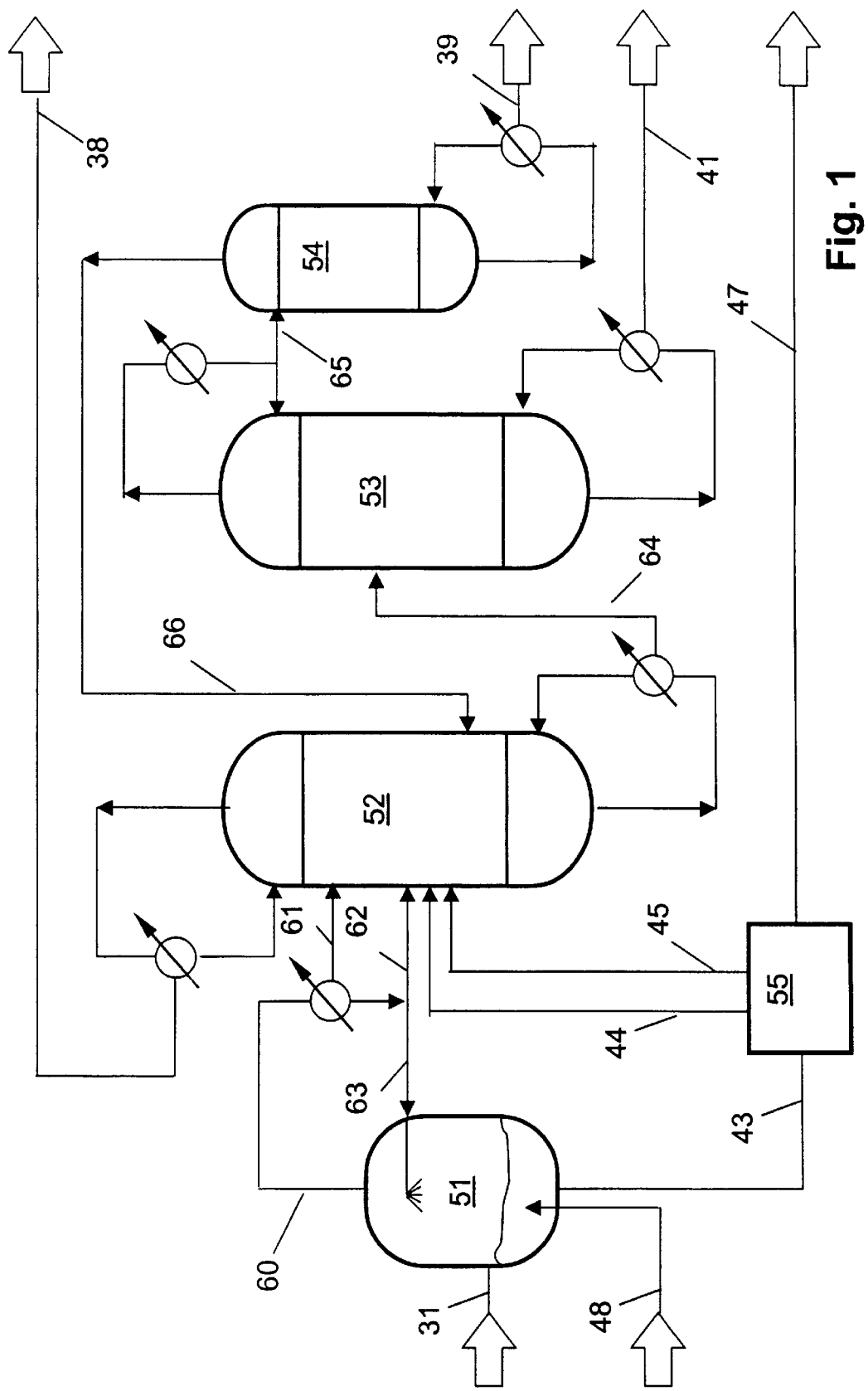

This is achieved in accordance with the invention in that:
   the further treatment steps are carried out by means of a rectifying zone, a distillation zone and a stripping zone
   and a cracking gas condensate which has an increased concentration of 1,2-dichloroethane (EDC) and is free from solids is used as quench liquid in the quench zone.

13 Claims, 3 Drawing Sheets

PROCESS FOR THE TREATMENT OF A CRACKING GAS FROM THE CRACKING OF 1,2-DICHLOROETHANE

The invention relates to a process for the treatment of a cracking gas produced in the cracking of 1,2-dichloroethane to give vinyl chloride.

In processes for the preparation of vinyl chloride by incomplete cracking of 1,2-dichloroethane (EDC), the EDC employed is usually evaporated in the first step, then, in a second step, the vapor formed is cracked pyrolytically at relatively high temperature, furthermore, in a third step, the entrained solids are separated off from the hot cracking gas produced in the second step, and subsequently the purified cracking gas is fed to distillative treatment.

The main products formed in the EDC cracking carried out in the second process step are hydrogen chloride (HCl) and vinyl chloride (VCM):

$$C_2H_4Cl_2 + heat \rightarrow HCl + C_2H_3Cl$$

By-products formed in traces are soot, chlorinated and unsaturated hydrocarbons and benzene. In order to limit the formation of these undesired by-products, the cracking temperature is held at a level which results in incomplete reaction of the EDC. The hot cracking gas produced by cracking in the second process step therefore also contains unreacted 1,2-dichloroethane (EDC) in addition to the main products hydrogen chloride (HCl) and vinyl chloride (VCM) and said by-products.

The cracking of EDC to give VCM is an endothermic process. It takes place in the gas phase in the form of pyrolysis. In industry, the pyrolysis is carried out without a catalyst under high pressure of from 1 to 3 MPa and at a temperature of from 450 to 600° C. However, work is also being carried out on catalytic processes which allow the pyrolysis to be carried out at lower pressure and lower temperature. The hot cracking gas produced by means of pyrolysis is formed at the pyrolysis temperature. It has to be conditioned so that it takes on a form which is suitable for the actual substance separation.

Before the actual substance separation of the cracking gas, the cracking gas heat is therefore utilized economically in one or more heat exchangers. In the process, the temperature of the cracking gas in the case of catalyst-free pyrolysis drops from between 480 and 540° C. to between about 180 and 280° C.

In a company publication published by Uhde GmbH in June 1995 with the title "Vinyl chloride plants/Hoechst process", the process usual hitherto for the treatment of the cracking gas is described.

In the process flow chart reproduced on page 11 of this company publication, it is shown that the precooled cracking gas is then cooled further and partially condensed in a quench. To this end, a cooled cracking gas condensate is introduced at the top of the quench zone. Two take-off streams containing product (VCM) are formed in the quench zone from the cracking gas and the cracking gas condensate introduced at the top:

the bottom discharge product is formed from the discharge product flowing out at the base of the quench zone;

the vapors flowing out at the top of the quench zone form the quench gas.

Only partial condensation of the cracking gas takes place in the quench zone. The liquid running out of the quench zone at the bottom, the so-called bottom discharge product, therefore contains as principal constituents 1,2-dichloroethane, vinyl chloride and high-boiling components and the solids, i.e. soot and/or coke.

The quench gas flowing out at the top of the quench zone as vapors contains hydrogen chloride, vinyl chloride and 1,2-dichloroethane as principal constituents. It is more or less free from the solids, i.e. free from soot and/or coke.

The cracking gas condensate employed as quench liquid is usually branched off from the condensed quench gas as a sub-stream, causing the formation of a quench liquid circuit.

The bottom discharge product and the partially condensed quench gas are then treated further.

EP-0 276 775-B1 gives the temperature of the catalyst-free pyrolysis as from 450 to 550° C. and pyrolysis pressures of from 0.5 to 3 MPa, but preferably from 1.6 to 2.6 MPa, and gentle measures for substance stream guidance.

DE-23 13 037-C3 describes a gentle arrangement of the evaporation.

Since it has proven advantageous to separate off the solids particles entrained by the cracking gas therefrom before distillative treatment of the cracking gas, this is usually carried out together with its cooling and partial condensation in the quench zone. In general, a quench device of simple design, which essentially consists of a vertical tank and a device for atomization of quench liquid in the interior of the tank, generally effects virtually complete purification of the cracking gas. The solids removed accumulate at the bottom of the quench zone.

U.S. Pat. No. 5,558,746 describes a quench column with plates which has a complex design and in which the solids are likewise removed from the circuit together with the bottom discharge product and then separated off. At the same time, the condensation of the cracking gas, which is usually carried out in an external device, is integrated into the quench column.

As is known, the pyrolysis of 1,2-dichloroethane is highly endothermic and characterized by the consumption of large amounts of thermal energy.

There has therefore been no lack of proposals for recovery of as much as possible of the heat present in the hot cracking gas from pyrolysis by means of heat transfer to other media:

EP-0 276 775-B1 indicates four variants for utilization of the cracking gas heat content for combinations of prewarming, evaporation and superheating of the EDC feed into the pyrolysis and for the generation of steam.

DE-31 47 310-C2 indicates the utilization of the heat content of the cracking gas for steam generation or for the heating of bottom forced-circulation evaporators in the distillative treatment in the preparation of VCM.

EP-0 180 995-B2 uses the product stream freed from solids in a quench column for generating steam and warming the EDC feed for the pyrolysis.

A common feature of the above-mentioned process variants is that the pyrolytically generated hot cracking gas is either cooled substantially to the vicinity of the dew point or even condensed at the dew point and therefore has to be re-heated in the subsequent distillative treatment. Even in the case of comprehensive use of the above-described heat recovery measures, there remains on the one hand a significant remainder of unutilized heat lost to the environment due to cooling and on the other hand a deficit of heat which has to be supplied again if necessary.

In the above-mentioned company publication with the title "Vinyl chloride plants/Hoechst process" published by Uhde GmbH in June 1995, the process usual hitherto for the distillative treatment of the cracking gas is described. In the process flow chart reproduced on page 13 of this company publication under the heading "VCM distillation", it is shown how the cracking gas taken off from the quench zone and freed from solids is then treated to give VCM, the distillative treatment of the pyrolytically generated cracking gas principally being directed toward the actual substance separation of this three-substance system with the three principal components HCl, VCM and unreacted EDC.

Three-substance systems require a comparatively complex separation apparatus for their separation. In addition, the present three-substance system also has a very broad boiling range, which means that the separation task requires solutions with a greater energy requirement than a mixture having a narrower boiling range.

Between the boiling points of HCl (minus 85° C.) and EDC (plus 83.5° C.), there is a temperature difference of 168.5° C. Owing to the very low boiling point of hydrogen chloride (HCl), cooling, preferably with cooling media which supply cold, must be carried out for the separation of HCl. In industry, the separation of HCl is carried out, for example, at 1.3 MPa absolute and −24° C. The industrial generation of cooling media which release cold is significantly more complex and also more complex than the provision of a cooling medium which has to achieve heat dissipation from the temperature level of the environment.

In the previous processes for distillative treatment, as described in German patent specifications DE-12 50 426, DE-19 10 854-C3 and DE-43 42 042-A1, the hydrogen chloride (HCl) is removed at the top of the first distillation column. In order to restrict the demand for cold to an economically sensible level, it is vital to feed the pyrolytically generated cracking gases into the first distillation column in substantially condensed form.

Furthermore, the bottom discharge product taken off from the first distillation column in the previous process shown in the above-mentioned company publication from Uhde GmbH essentially contains the VCM regarded as product and the unreacted EDC. This bottom discharge product is fed to the second column. In the second column, it is separated into unreacted EDC and VCM. However, the VCM distilled off at the top of the second column contains unavoidable fractions of HCl, which have to be separated off in a third column using additional supply of energy.

The cause of the presence of HCl in the vapors taken off at the top of the second distillation column in the previous process is due, in particular, to the thermal instability of the EDC. By means of suitable, sufficiently sensitive analytical methods, the decomposition products HCl and VCM can be detected in pure EDC even at temperatures of from 100° C. With increasing temperature and increasing residence time, the amount of HCl and VCM formed also increases.

The previous process therefore has considerable potential for further improvements. Firstly, the previous distillation sequence with removal of HCl in the first step does not allow substantial utilization of the heat present in the pyrolytically generated cracking gas, since the cracking gas must be substantially condensed in order to minimize the demand for cold energy.

Secondly, the removal of the VCM from all high-boiling components in the second step requires considerable expenditure of energy, together with the necessity, owing to the thermal instability of the EDC, of removing newly formed HCl in an additional purification step.

This is where the process according to the invention starts and has the object of improving the existing process by separating HCl and VCM off from all higher-boiling components in the first step of the distillation sequence and only carrying out the unavoidable use of coolant in the subsequent step for the removal of the HCl.

It thus becomes possible in accordance with the invention to avoid, in particular, the energy losses which usually occur due to substantial condensation of the quench gas and its reheating for the purpose of distillative separation and, through circulating the unreacted EDC at a higher temperature level, subsequently to increase the original conversion of the pyrolytic cracking of EDC.

To this end, the invention proposes a process for the treatment of the cracking gas, in which the cracking gas employed has been formed from the pyrolysis of 1,2-dichloroethane (EDC), the cracking gas is split into its principal components hydrogen chloride (HCl), vinyl chloride (VCM) and unreacted 1,2-dichloroethane (EDC), and these principal components arise in substantially pure form, where, in the first step of the treatment of the cracking gas, the solids are separated off therefrom in a quench zone, and the process is characterized in that:

the further treatment steps are carried out by means of a rectifying zone, a distillation zone and a stripping zone and a solids-free cracking gas condensate which has an increased concentration of 1,2-dichloroethane (EDC) is used as quench liquid in the quench zone.

Embodiments of the invention arise from the further claims.

In the preferred embodiment, the invention relates to a process for the treatment of the cracking gas that arises in the non-catalytic thermal cracking of 1,2-dichloroethane to give vinyl chloride with a temperature of from 480 to 540° C. and a pressure of from 0.5 MPa to 3 MPa and is optionally cooled to a temperature of from 180 to 280° C. in a heat recovery and is passed with this temperature into a quench zone, in which it is cooled and washed with EDC-enriched cracking gas condensate, where the process is characterized in that:

1 to 2% by weight, based on the amount of cracking gas employed, are removed in liquid form as solids-loaded bottom discharge product at the bottom of the quench zone, the remaining amount (cracking gas used plus quench liquid minus bottom discharge product) is removed in gas form as purified quench gas at the top of the quench zone, the quench gas obtained here is passed directly downwards into a rectifying zone, and the quench gas is separated therein into a distillate and a bottom product, which is free from components which boil higher than VCM, and an EDC-enriched bottom product, the bottom product arising in the rectifying zone is discharged, and the said solids-free cracking gas condensate, which is enriched with 1,2-dichloroethane (EDC), is thus obtained, and it is separated into two sub-streams, and, as the first sub-stream, the preliminary fraction for the stripping zone is obtained and, as the other sub-stream, the EDC-enriched, solids-free cracking gas condensate that is fed back into the quench zone in order to treat the cracking gas to be treated with it therein as coolant and washing agent is obtained;

and in that the distillate and the preliminary fraction are fed separately to the further distillative treatments and the bottom discharge product coming from the quench zone which is loaded with the solid to be removed is fed to another treatment.

In the process according to the invention, the distillate intended for the first further distillative treatment and the preliminary fraction intended for the other further distillative treatment are obtained free from any solids loading. The significant advantage inherent in the previous process therefore also arises in the process according to the invention, namely that it is advantageous if it can be avoided that the solids emanating from the cracking gas, such as soot and/or coke, are able to enter the apparatuses of the further distillative treatments and deposit therein. The formation of blockages in practical operation of the apparatuses is countered in a simple manner of this type.

This is because, as already described above, the solids removed in the purification are, in the previous process, formed exclusively at the bottom of the quench zone, which enables simple concentration and disposal of the solids suspension.

It has proven particularly surprising in the process according to the invention that the quench gas entering the rectifying zone has, at an EDC cracking rate of at least 50% in the prior pyrolysis, such a composition that it is sufficient, at an absolute pressure of at least 1.9 MPa above the uppermost plate of the rectifying zone, to charge the reflux condenser of the rectifying zone merely with cooling water running at the ambient temperature in order to obtain a vigorous reflux into the rectifying zone. Furthermore, it has proven surprising in the process according to the invention that, with at least 25 theoretical plates for the rectifying zone and a reflux ratio of 1.5 to 2.5, firstly top vapor, reflux and distillate streams which are free from all components which boil higher than VCM, such as, for example, chloroprene or EDC, are obtained, and that secondly, the discharge product from the bottom plate of the rectifying zone is enriched with EDC to greater than 80% by weight since the EDC is that principal component of the three-substance mixture which has the highest boiling point.

It arises in accordance with the invention that the thermal instability of the EDC in a sub-stream which forms the preliminary fraction in the stripping zone are unharmful in respect of the purity requirements of the product VCM. If, as a consequence of the thermal instability, HCl and VCM form as decomposition products in the stripping zone, they are formed at the top of the stripping zone and, in accordance with the invention, are fed back from there into the rectifying zone. Gentle performance of the distillation, as was appropriate in the second step of the distillation in the previous process, is no longer necessary in accordance with the invention. In particular, the pressure and temperature at the bottom of the stripping zone can be increased without harm. In the rectifying zone, the decomposition products are again removed at the top and passed over into the distillation zone together. However, thermal instability cannot take effect in the distillation zone since the distillation zone is operated well below 100° C. in all of its separation stages.

One embodiment of the process according to the invention therefore proposes that the distillative treatment of the preliminary fraction takes place in the stripping zone, the 1,2-dichloroethane (EDC) recovered in enriched form is taken off with the bottom product formed therein, and the top product formed therein is fed back into the rectifying zone.

Another embodiment of the process according to the invention therefore proposes that the distillative treatment of the distillate is carried out in the distillation zone, the vinyl chloride (VCM) separated off is taken off in highly enriched form with the bottom product formed therein, and the hydrogen chloride (HCl) is recovered in enriched form with the top product formed therein. For reasons of safe operation, in particular in order to intercept HCl breakthrough into the VCM product in the case of non-optimum operation of the column, a separate fine purification zone as in the previous process is appropriate.

The process according to the invention utilizes the heat content of the pyrolytically generated cracking gas virtually completely, in a particularly advantageous manner, through the quench gas being fed directly downwards into the rectifying column as vapor to be treated distillatively. Furthermore, the connection according to the invention of the quench zone to the newly arranged distillation sequence of the treatment results in circulation of the unreacted EDC at longer residence time at higher temperatures, for which reason, in combination with the thermal instability of the EDC, an unexpected increase in yield occurs without the need for an additional purification step.

An advantageous embodiment of the process can consist of the following steps:

firstly, the gas mixture to be separated can be present with temperatures of from 85 to 540° C. and with a pressure of from 0.1 MPa to 3.0 MPa, secondly, the gas mixture to be separated is, before entry into the first distillation column, fed in gas form beneath the internals of a rectifying zone, thirdly, a mixture of HCl, VCM and components which boil lower than VCM is taken off at the top of the rectifying zone and passed as feed to a distillation zone, fourthly, the bottom product from the rectifying zone is a mixture which consists of EDC as principal component and HCl, VCM and components which boil higher than VCM as secondary components and which is fed to a stripping zone as a sub-stream, if quench liquid is necessary for prior separation of solids from the gas mixture employed, or as a full stream, fifthly, the top product from the rectifying zone is separated in the distillation zone into high-purity VCM, which is formed as bottom product in the distillation zone, and substantially pure HCl, which consists of HCl and components which boil lower than VCM and is formed at the top of the distillation zone, and sixthly, the mixture running in from the bottom of the rectifying zone is separated in the stripping zone, substantially pure EDC being taken off at the bottom of the stripping zone together with all components boiling higher than VCM and with an only very low content of HCl and VCM, and a mixture consisting of EDC and HCl and VCM introduced into the feed and HCl and VCM newly formed due to the thermal instability of EDC being obtained at the top of the stripping zone and being fed back into the rectifying zone for the purposes of further treatment.

The process is also distinguished by the fact that a gas mixture employed in the rectifying zone, freed from solids, but provided with relatively low pressure, is brought, using a compression unit, to a pressure which ensures economical operation of the rectifying zone.

It may be advantageous for the stripping zone to be operated either at lower or at higher pressure than the pressure used in the rectifying zone. In the case of a lower pressure in the stripping zone, the pressure increase of the top product of the stripping zone which is fed back to the rectifying zone can either be carried out by total condensation of this top product with subsequent pressure increase via a pump or in the gaseous state by means of a compression unit. In the case of a higher pressure in the stripping zone, the pressure matching is carried out by means of a pump in the stripping zone feed originating from the bottom of the rectifying zone.

The process may also be distinguished by one or more bottom forced-circulation evaporators of the distillation zone being heated by means of the bottom product from the stripping zone, where it may likewise be provided that the bottom product from the distillation zone is fed through an optionally connectable fine purification zone, a high-purity product stream being taken off at the bottom of the fine purification zone, and the top product from the fine purification zone being fed back into the distillation zone.

The process may also be distinguished by the use of a gas mixture charged with solid particles, such as, for example, soot, as is usually produced in the non-catalytic thermal cracking of 1,2-dichloromethane to give vinyl chloride at a temperature of from 480 to 540° C. and a pressure of from 0.5 MPa to 3.0 MPa and is optionally cooled to a temperature of from 180 to 280° C. in a heat recovery step. In the case of catalytic cracking of 1,2-dichloroethane to give vinyl chloride, the gas mixture employed may also be present at lower temperatures of up to 85° C. and at a lower pressure of up to 0.1 MPa.

In the case of solids charging of the gas mixture employed, the process is characterized in that a quench zone for washing out the solids particles and quench bottom product treatment for the recovery of EDC, VCM and HCl are provided before the separation devices (rectifying zone, distillation zone and stripping zone) described in claim 1.

The quench zone is characterized in that a sub-stream of the bottom discharge product from the rectifying zone is employed as quench liquid after cooling.

The quench zone is furthermore characterized in that
firstly, from 1 to 20% by weight, based on the amount of gas mixture employed, are produced in liquid form at the bottom of the quench zone as solids-loaded bottom discharge product and are treated further in the quench bottom product treatment,
secondly, the remaining amount (gas mixture employed plus quench liquid minus bottom discharge product) is produced at the top of the quench zone in gas form as purified quench gas and is fed into the rectifying zone either directly or via a compression unit according to claim 2,
thirdly, the quench zone can be defined in equipment terms either as an independent apparatus or alternatively in the form of a component integrated into the rectifying zone, and
fourthly, the quench zone is designed in equipment terms as an independent apparatus if the compression unit according to claim 6 is employed.

The quench bottom product treatment is characterized in that the solids-loaded bottom discharge product is thickened by stepwise decompression and evaporation to the extent that the residual stream obtained remains pumpable, substance streams which contain primarily EDC and also HCl and VCM being obtained during the evaporation and being fed into the stripping zone in order to recover its useful substances.

The quench bottom product treatment is furthermore characterized in that
firstly, in the first step, decompression is carried out to a pressure which is somewhat above the pressure in the stripping zone,
secondly, a gas stream is obtained by supplying heat to the first step and is fed directly into the stripping zone,
thirdly, the remaining liquid from the first step is decompressed to virtually atmospheric pressure in the second step, and
fourthly, a gas stream is obtained by supplying heat to the second step and, after total condensation, is brought to the pressure of the stripping zone by means of a pump and fed into this zone.

It is also advantageous that the gas mixture employed in the quench zone is provided with a lower pressure than the pressure prevailing in the stripping zone, and that, instead of the decompression in the first step of the quench bottom product treatment, the quench bottom product is brought to a somewhat higher pressure than the pressure prevailing in the stripping zone by means of a pump and/or in that the gas mixture employed originates from an EDC cracking process in which external EDC evaporation is used and an EDC elutriation stream is produced, the EDC elutriation stream being included in the quench bottom product treatment and
is either fed into the quench bottom product
or, in the first step of the quench bottom product treatment, the external heat supply is replaced by feeding-in with flash evaporation.

Figure 2:
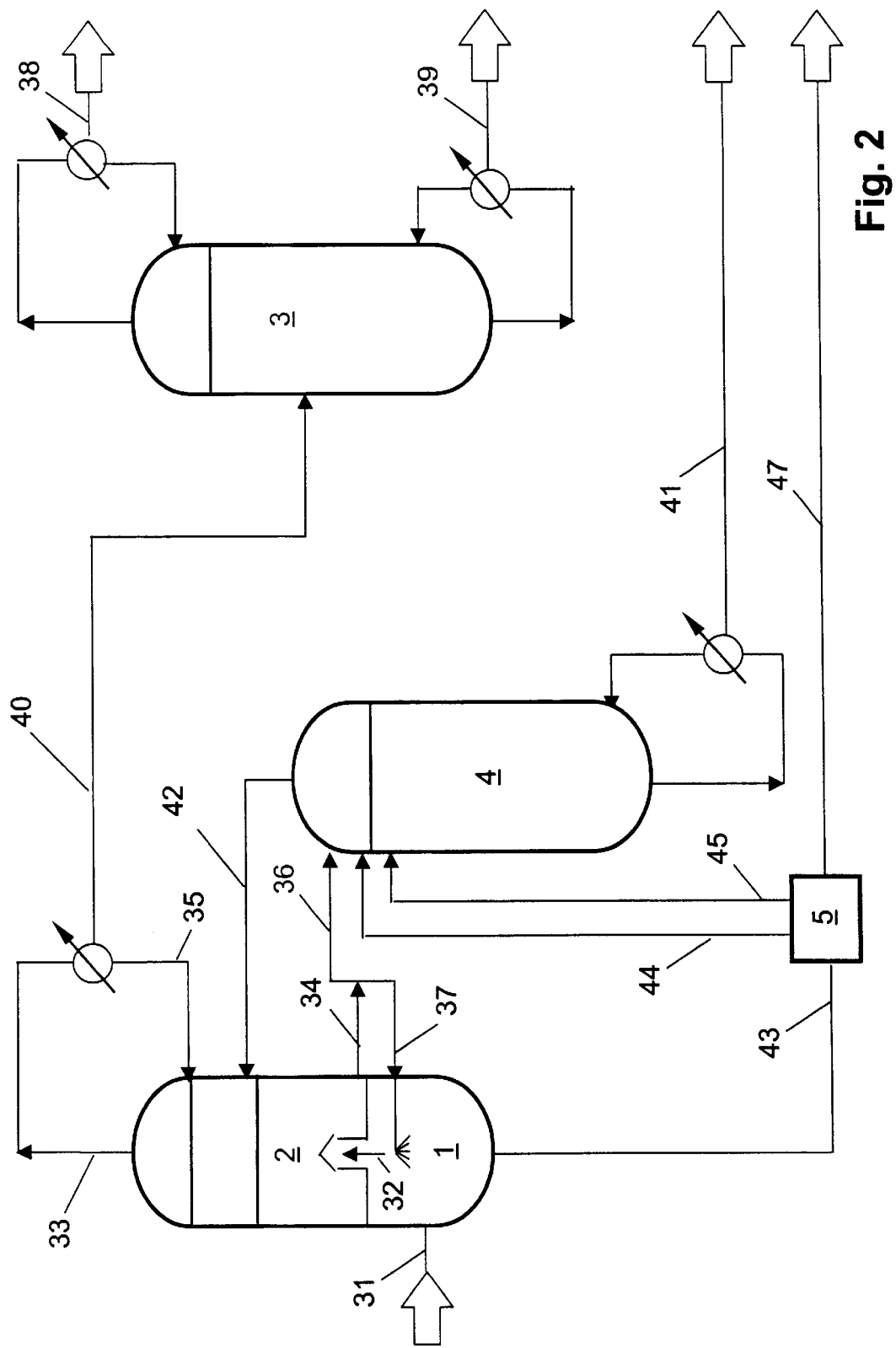
Figure 3:
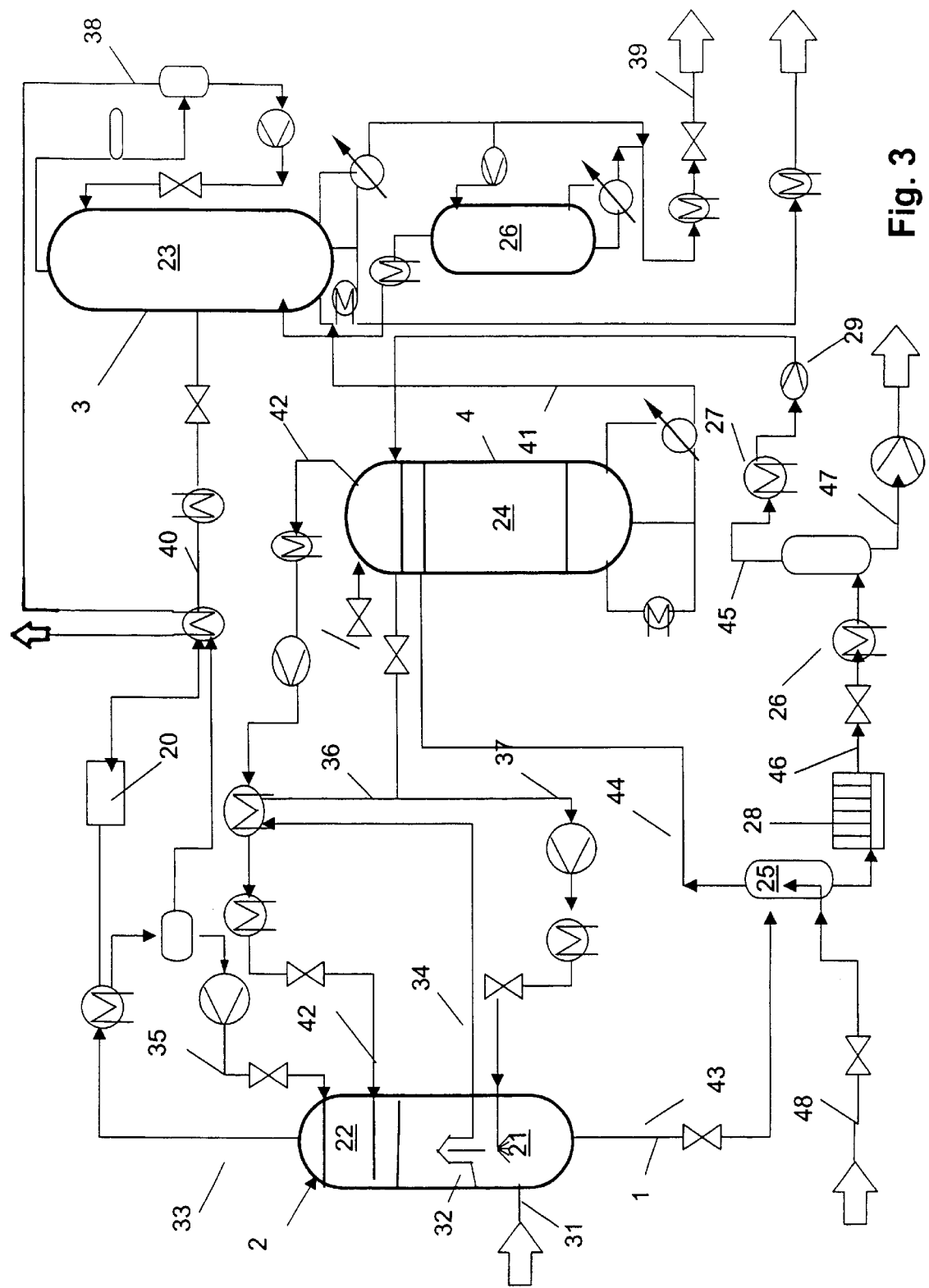

The process of the invention is explained in greater detail below with reference to the attached drawings, in which:

FIG. 1 shows in a block flow chart the connection of the separation devices of the previous cracking gas treatment process, FIG. 2 shows in a block flow chart the connection of the substance separation zones which interact in the cracking gas treatment according to the invention, and FIG. 3 shows a process flow chart in which one illustrative embodiment of the many other possible embodiments of the equipment design of the present invention is represented.

FIG. 1 shows a simplified block flow chart of the quench system 51, the HCl column 52, the VCM column 53, the VCM stripper 54 and the quench bottom product treatment 55 of the previous process.

The cracking gas 31 employed, produced by non-catalytic pyrrolysis of 1,2-dichloroethane (EDC), consists of the principal components HCl, VCM and unreacted EDC. It is provided at temperatures of from 180 to 540° C., preferably from 230 to 280° C., and with a pressure of from 0.5 MPa to 3 MPa, preferably with a pressure of approximately 2 MPa. The cracking gas 31 employed preferably originates from a process in accordance with EP-0 276 775-B1.

In the quench system 51, the cracking gas is cooled by means of the quench liquid 63 and freed from solids. The quench liquid 63 consists of a sub-stream of the cracking gas condensate obtained by cooling the quench top vapor 60. In the Uhde GmbH publication corresponding to the process, an elutriation stream 48 forming in the EDC evaporation in accordance with EP-0 276 775-B1 is furthermore fed to the bottom of the quench system 51. The solids-loaded quench bottom discharge product 43 is thickened further in the quench bottom product treatment 55. The substantially condensed quench top vapor 60 is passed into the HCl column 52 as a liquid stream 62, which is formed from the cracking gas condensate after removal of the quench liquid 63, and as a gas stream 61, together with the product streams 44 and 45 recovered in the quench bottom product treatment 55 and comprising predominantly EDC.

The solids, such as coke, and residual stream 47 from the quench bottom product treatment 55, which still contains sufficient liquid, predominantly EDC, for the purpose of pumpability, is fed to a separate further processing step.

The gaseous product stream 38, which consists of predominantly pure HCl gas, is taken off at the top of the HCl column 52. In order to generate reflux for the HCl column 52, cold energy must be employed. The HCl column is preferably operated at the top with 1.3 MPa absolute and −24° C. In order, for economic reasons, to restrict the consumption of expensive cold energy, the feed must be in substantially condensed form. The heat withdrawn from the system in this way in accordance with FIG. 1 must be re-introduced into the bottom forced-circulation evaporator of the HCl column 52.

The bottom discharge product 64 from the HCl column 52, which consists of the principal components EDC and VCM, is fed into the VCM column 53, where it is separated into the liquid top product 65, consisting of EDC-free VCM, and the bottom product 41, principally consisting of EDC. The product stream 41 is worked up separately, and the recovered EDC is re-introduced into the pyrolysis.

In order, for economic reasons, to be able to generate the reflux for the VCM column using cooling water, the column is operated at a top pressure of from 0.6 to 0.7 MPa absolute. This inevitably results in bottom temperatures of approximately 160° C., at which EDC is already noticeably cracked into HCl and VCM. The majority of the newly formed HCl is recovered in the top product 65 of the VCM column 53.

In order to remove the HCl, the top product 65 from the VCM column 53 is subjected to fine purification in the VCM stripper 54. At the bottom of the VCM stripper 54, high-purity VCM is taken off in the product stream 39 regarded as the main product. The top vapor 66 of the VCM stripper 54 consists principally of VCM and contains all the HCl introduced in the feed stream 65 to the VCM stripper 54.

The top vapor 66 of the VCM stripper 54 is fed back to the HCl column 52.

FIG. 2 shows in a simplified block flow chart the quench zone 1, the rectifying zone 2, the distillation zone 3, the stripping zone 4 and the quench bottom product treatment 5 of the process according to the invention.

Compared with the previous process shown in FIG. 1, the cracking gas 31 employed and its separation into product streams 38, 39, 41 and 47 are unchanged.

The cracking gas 31 consists, as before, of the principal components HCl, VCM and unreacted EDC and is, as before, separated into substantially pure HCl gas (product stream 38), high-purity VCM, which is regarded as the main product (product stream 39), product stream 41, which consists principally of unreacted EDC, and the solids-containing, substantially thickened product stream 47.

Novel aspects according to the invention are the modified arrangement of the treatment devices and the resultant considerable reduction in energy consumption.

The cracking gas 31 is no longer, as before, washed with cracking gas condensate in the quench zone 1, but instead with a sub-stream 37 of the bottom discharge product from the rectifying zone 2. The quench liquid 37 in the process according to the invention differs from the quench liquid 63 in the previous process through a considerably higher content of EDC.

The quench top vapor 32 in the process according to the invention is no longer condensed, but instead fed directly into the rectifying zone 2 as replacement for a bottom forced-circulation evaporator.

The rectifying zone 2 has the task, as a new element in the process according to the invention, of removing the principal components HCl and VCM, which are free from components boiling higher than VCM, at the top (top product 40). By contrast, the bottom discharge product 34 from the rectifying zone 2 contains principally EDC in addition to HCl and VCM.

The top product 40 from the rectifying zone 2 is fed into the distillation zone 3.

The distillation zone 3 has the task, as a new element in the process according to the invention, of separating the principal components HCl and VCM into substantially pure HCl gas as top product 38 and high-purity VCM as bottom product 39.

The quench bottom product treatment 5 in the process according to the invention has the same functionality as the quench bottom product treatment 55 in accordance with FIG. 1 of the previous process.

The recovered product streams 44 and 45 from the quench bottom product treatment 5 are fed in at the top of the stripping zone 4 together with the feed stream 36 formed from the bottom discharge product 34 from the rectifying zone 2 minus the necessary amount of quench liquid 37 to the quench zone 1.

The stripping zone 4 has the task, as a new element in the process according to the invention, of removing unreacted EDC in the bottom product together with secondary components boiling higher than VCM in the product stream 41.

The top vapor 42 from the stripping zone 4 contains all principal components (HCl, VCM and EDC) and is fed back into the rectifying zone 2 for further separation.

Owing to the requisite temperatures, partial decomposition of the EDC to HCl and VCM occurs in the stripping zone 4, as in the VCM column 53 according to FIG. 1 of the previous process.

Owing to the substance stream feed, which is altered in accordance with the invention as shown in FIG. 2, with return of the stream 42 into the rectifying zone 2, the unavoidable thermal instability of the EDC no longer requires additional complexity in a fine purification zone, but is instead advantageous with respect to an increase in the yield of VCM.

FIG. 3 shows in a detailed process flow chart a preferred embodiment of the process according to the invention. The solids-loaded cracking gas feed 31 is fed into the lower part of a quench device 21. The quench device 21 may be designed as a vertically arranged tank, but a preferred embodiment consists of the lower, internals-free space of a distillation column 21, the free space being arranged beneath the distillation internals, such as plates or packing. A feed line for the quench liquid is located in the upper part of the free space of the quench device 21. The feed line runs into a suitable distributor device in the interior of the free space, by means of which uniform charging of the entire free cross section takes place, preference being given to a system consisting of one or more nozzle crowns. The pressure in the quench device 21 is determined by the pressure of the inflowing cracking gas feed 31.

The amount of quench liquid is set so that complete washing-out and retention of the solids particles present in the inflowing cracking gas 31 is achieved. A connector for discharging the quench liquid loaded with solids particles is located at the bottom of the quench device 21. The part of the quench device 21 which terminates the quench zone 1 at the top is, in a separate tank solution, designed as a lid with connectors, but preferably, in the case of integration of the quench zone 1 into a distillation column 23, as a collecting tray with gas passage for discharging the gaseous quench gas stream 32 freed from solids. By means of this passage, the quench gas 32 is transferred directly from the quench zone 1 into the rectifying zone 2.

In the rectifying zone 2, the HCl and VCM predominantly separated off from the quench gas 32 are produced together at the top of the column 22. The rectifying zone 2 does not require the introduction of any external energy for heating. The heating of the rectifying zone 2 takes place autothermally through utilization, for the substance separation work to be supplied, of the heat content of the quench gas 32, which is introduced into the rectifying zone 2 from the bottom beneath the lowermost part of the distillation internals, which consist of commercially available plates or packing. The pressure of the quench gas 32 freed from solids has a crucial effect on the determination of the pressure in the rectifying zone 2.

Owing to the use of exclusively cooling water for the reflux generation, a pressure of at least 1.9 MPa in the rectifying zone 2 is particularly economical. This arises if the cracking gas 31 preferably originates from the process according to EP 0 276 775 B1. If the cracking gas 31 originates from other processes with a lower pressure, particularly from catalytic pyrolysis, an economic analysis will determine whether the reflux generation takes place at lower pressure by the use of cold or whether, in an alternative embodiment according to the invention of the quench device 21 and the rectifying zone 22 in the form of separate apparatuses, a compression step is inserted for the quench gas 32.

The reflux in the rectifying zone 2 is dimensioned such that all components boiling higher than VCM are held back. The cooling medium used for one or more top condensers is cold, cooling brine and/or preferably cooling water, in accordance with the pressure conditions. The top vapor 33 from the rectifying zone 2 is preferably only condensed partly, so that entrained water can be separated off in the gas phase which remains by means of a suitable drying device 20, preferably in accordance with patent specification DE-43 42 042-A1. In the preferred apparatus embodiment of the rectifying zone 2 as attachment to the quench device 21, the bottom product 34 from the rectifying zone 2, essentially consisting of EDC and HCl and VCM dissolved therein, is discharged from the rectifying zone 2 by means of baffle plates, but otherwise via a base connector.

The amounts of HCl and VCM dissolved in the bottom product 34 from the rectifying zone 2 are recovered in the process according to the invention and fed into the rectifying zone 2. The process proposes that the return stream 42 can either be in gas form or preferably in liquid form. A gaseous return stream 42 is fed directly into the rectifying zone 2 beneath the internals. In the preferred case of a liquid return stream 42, the separating column 22 acting as rectifying zone 2 comprises an additional mixing zone beneath the feed connector for the return stream 42.

The bottom product 34 discharged from the rectifying zone 2 is cooled and then separated into two sub-streams.

The first sub-stream of the cooled bottom product 34 forms the preliminary fraction 36 for the stripping zone 4 and is passed over into the stripping zone 4 described below.

The other sub-stream of the cooled bottom product 34 forms the quench liquid which is sprayed in at the top of the quench zone 1 as EDC-enriched cracking gas condensate 37 and with which, as coolant and washing agent, the cracking gas 31 is treated in the quench zone 1. A further water-cooled heat exchanger is utilized only for starting up the plant and in the event of a breakdown for temporary additional cooling of the quench liquid 37.

The top vapor 33 from the rectifying zone 2, which comprises the principal components HCl and VCM, is, in accordance with the invention, after total condensation or preferably after partial condensation and after removal of the return 35, fed as remaining feed stream 40 to a distillation zone 3, which is designed as a conventional distillation column 23 with rectifying zone above and stripping zone beneath the feed. The distillation internals consist of commercially available plates or packing. Substantially pure HCl 38 is taken off at the top of the column 23, and high-purity VCM 39 is taken off at the bottom after optionally passing through the fine purification zone 26. In contrast to the previous process (VCM stripper 54 in FIG. 1), the fine purification zone 26 need not be operated constantly, but instead represents a safety device with which any threatening HCl breakthrough into the VCM product stream 39 is avoided only in the case of non-optimum operation of the distillation zone 3. In the case of optimum operation of the distillation zone 3, the fine purification zone 26 is bridged, as shown in FIG. 3 by means of the dashed line. The column bottom product is heated by means of one or more forced-circulation evaporators, one forced-circulation evaporator of which is preferably heated by means of steam in order to establish the VCM product quality. It is furthermore preferred additionally to heat one or more forced-circulation evaporators by means of suitable product streams. The pressure in this distillation zone 3 is determined by the coolant employed for the reflux generation, preference being given to refrigerants, such as, for example, evaporating propylene. For reasons of economical use of refrigerant, it may be appropriate to precool the feed 40, preferably in countercurrent with the top product, but alternatively using an additional cooling device. The pressure in the distillation zone 3 is preferably below the pressure in the rectifying zone 2.

The process according to the invention can also treat cracking gas 31 which has been produced by pyrolysis of 1,2-dichloroethane (DDC) and is transferred as feed at relatively low pressure. The pressure in the rectifying zone 2 thus likewise adopts relatively low values. In this case, the feed 40 to the distillation zone 3 can be totally condensed by means of a suitable coolant and brought to a higher pressure by means of a pump in order to achieve economical separation of HCl and VCM.

The first cooled sub-stream of the bottom product 34 from the rectifying zone 2 forms the preliminary fraction 36 for the stripping zone 4. The preliminary fraction 36 is fed into the stripping zone 4 at the top, more precisely above the distillation internals. In this upper space of the stripping zone 4, a mixing zone is arranged for the accommodation of further substance streams in the process according to the invention. These further substance streams are fed back from other treatments since, in addition to EDC, they also comprise HCl and VCM. Due to their return into the stripping zone 4, the relevant amounts of the principal components originating from the cracking gas 34 are not lost.

The lower sub-space of the stripping zone 4 is provided with the distillation internals. In this lower sub-space of the stripping zone 4, removal of the unreacted EDC present in the preliminary fraction 36 of the stripping zone 4 takes place. The unreacted EDC is obtained substantially free from HCl and VCM as the bottom product 41 from the stripping zone 4.

The distillation internals in the stripping column 24 consist of commercially available plates or packing. The column bottom product is heated by means of one or more forced-circulation evaporators, of which one forced-circulation evaporator is preferably heated with steam in order to set the lowest possible VCM loss in the bottom product. It is furthermore preferred additionally to heat one or more forced-circulation evaporators by means of suitable product streams in order to save energy, for example in accordance with patent specification DE-41 31 576-A1.

The gaseous top product 42 from the stripping zone 4 comprises recovered HCl and VCM and unreacted EDC. The top product 42 from the stripping zone 4 is fed back into the rectifying zone 2. The pressure set in the stripping zone 4 ensures economical operation. It is thus achieved that firstly the energy costs are minimized and secondly the top product 42 is held at a temperature level above 100° C. At such a raised top temperature of the stripping zone 4, the yield of VCM is increased since partial thermal decomposition of the EDC to VCM and HCl then takes place on its own without further action.

The pressure in the stripping zone 4 is preferably set to low values compared with the rectifying zone 2 so long as the cracking gas 31 employed is produced by the method described in EP-0 276 775-B1 and is in the preferred pressure range therein of from 1.6 to 2.6 MPa. A method for increasing the pressure of the gaseous top product 42 taken off from the stripping zone 4 consists in total condensation of the top product 42, subsequently increasing its pressure by means of a pump and subsequently heating it in countercurrent with the bottom product 34 from the rectifying zone 2. In a variant which can be carried out as an alternative, the gaseous top product 42 from the stripping zone 4 is brought, by means of a compression unit, to a pressure which allows the recycling of the top product 42 from the stripping zone 4 into the rectifying zone 2, which is operated at a higher pressure. A further steam-heated heat exchanger is only additionally used for starting up the plant and for temporary heating in the event of a breakdown.

However, the pressure in the stripping zone 4 can also be set to higher values compared with the pressure in the rectifying zone 2. In this case, the preliminary fraction 36 from the stripping zone 4 which is passed over from the rectifying zone 2 into the stripping zone 4 is brought to the higher pressure prevailing in the stripping zone 4 by means of a pump.

The bottom product from the quench zone 1, the bottom discharge product 43, is treated in the process according to the invention with the aim of recovering HCl and VCM. This is carried out by means of the successive process steps of filtration, stepwise decompression and partial evaporation.

If the process in accordance with the present invention is used together with the process in accordance with patent specification EP-0 276 775-B1, a liquid elutriation stream 48 essentially consisting of pure EDC is, in the variant with external EDC evaporation, formed in an evaporation zone whose temperature is below or virtually at the boiling point of pure EDC. This evaporation zone operates at a higher pressure than the pressure set in the quench zone 1.

This elutriation stream 48, by means of which it is intended to reduce the amount of precursors or nuclei for the soot formation which occurs in pyrolytic EDC cracking in the EDC to be evaporated, is included in the quench bottom product treatment. In the previous process in accordance with FIG. 1, the elutriation stream 48 is fed into the quench device 51 beneath the liquid level of the quench bottom product in order to evaporate principally dissolved HCl and VCM.

Furthermore in the previous process represented in FIG. 1, the bottom discharge product 43 from the quench 51 is filtered, decompressed to a somewhat higher pressure than that of the HCl column 52 and heated by means of a steam-heated heat exchanger in order to obtain a gas stream 44 containing HCl, VCM and EDC, which is fed to the HCl column 52 in order to recover the products.

In accordance with the invention, another form of the feeding-in of the elutriation stream 48 is preferred in the process indicated here, this form of feeding-in being of simple design such that, through the use of only one one-step decompression evaporation of the elutriation stream 48 into a tank 25, the first heat exchanger in the previous process, including the associated heating energy consumption, is unnecessary. The design according to the invention proposes that the bottom discharge product 43 from the quench zone 1 is decompressed directly into a tank 25, and the elutriation stream 48, which is obtained in predominantly gas form after decompression, is fed into the liquid phase of the tank 25 by means of a suitable device.

The evaporated part of the bottom discharge product 43 is separated off from the bottom discharge product 43 as a first gas stream 44 and is fed into the stripping zone 4 beneath the mixing zone. The remaining first liquid stream 46 is subsequently freed from removable solids in the filtration unit 28 and decompressed to a pressure which is somewhat above atmospheric pressure. After further heat has been supplied to the first liquid stream 46 in the heat exchanger 26 and thus a further part of the original bottom discharge product 43 has been evaporated, a second gas stream 45 is separated off. The remaining second liquid stream 47 is substantially free from HCl and VCM and is fed to a treatment which is not part of the process according to the invention. The second gas stream 45 is totally condensed by means of cooling water in the heat exchanger 27, brought to the pressure of the stripping zone 4 by means of a pump 29 and fed into the stripping zone 4 above the distillation internals.

The process according to the invention is capable of treating a cracking gas 31 produced industrially either by means of catalyst-free pyrolysis or by means of catalytic pyrolysis. The hot cracking gas 31 produced by means of pyrolysis consists of its principal components HCl, VCM and unreacted EDC. In the case of a process for the thermal cracking of 1,2-dichloroethane in which the formation of solids, such as soot and/or coke, is avoided, the plant parts 1 (quench zone) and 5 (quench bottom product treatment) are unnecessary in the process according to the invention shown in FIG. 2 as a block flow chart. In the case of an atmospheric-catalytic process for the thermal cracking of EDC which operates without solids, the process according to the invention should be provided with a compression step before entry of the cracking gas 31 into the rectifying zone 2.

The economic advantages which arise on use of the process according to the invention consist in that, with approximately constant consumption of cold and pump energy, and approximately constant capital expenditure costs, the consumption of steam and cooling water is significantly reduced.

In the preferred use in accordance with FIG. 3, the following consumption values arise for a cracking gas and an EDC elutriation stream from a process in accordance with EP-0 276 775-B1 compared with the previous process in accordance with FIG. 1:

constant consumption of cold energy, an increase in the net pump output by 5%, a reduction in the consumption of medium-pressure steam by 67%, a reduction in the consumption of low-pressure steam by 80% and a reduction in the consumption of cooling water by 36%.

Based on a 100,000 tonnes per year VCM plant with an operating time of 8000 hours per year, this means annual savings of 26,700 tonnes of medium-pressure steam and 20,280 tonnes of low-pressure steam.

What is claimed is:

1. A process for the treatment of a cracking gas formed by the pyrolysis of 1,2-dichloroethane, the process comprising the steps of:

splitting 1,2-dichloroethane into a mixture of hydrogen chloride, vinyl chloride monomer, unreacted 1,2-dichloroethane, and solid by-products;

separating the solid by-products from the mixture in a quench zone;

recovering top products and bottom products at the top or bottom of the quench zone, respectively;

sequentially treating the solids-free top products mixture recovered from the quench zone in a rectifying zone, a distillation zone, and a stripping zone to yield a solids-free cracking gas condensate, the condensate having a concentration of 1,2-dichloroethane higher than that in the mixture applied to the quench zone; and using the cracking gas condensate as a quench liquid in the quench zone.

2. The process according to claim 1, wherein the distillative treatment of the distillate removed from the quench zone is carried out in the distillation zone, the highly enriched vinyl chloride monomer is separated and removed with the bottom product formed therein, and the hydrogen chloride is recovered in an enriched form with the top product formed therein.

3. The process according to claim 1, wherein the solids-free gas mixture fed to the rectifying zone, is maintained at a low pressure, by use of a compression unit, to ensure economical operation of the rectifying zone.

4. The process according to claim 1, wherein the stripping zone is operated at a pressure either higher or lower than the pressure used in the rectifying zone.

5. The process according to claim 1, wherein the stripping zone yields products that are recovered at the top and the bottom of the stripping zone, and one or more bottom forced-circulation evaporators of the distillation zone are heated by means of the bottom product from the stripping zone.

6. The process according to claim 1, wherein the gas mixture yields products that are recovered at the top and the bottom of said distillation zone, and further comprising the steps of:

feeding the bottom product from the distillation zone through an optionally connectable fine purification zone;

removing from the fine purification zone a high-purity product stream from the bottom of the fine purification zone, and the top product from the top of the fine purification zone; and feeding said top product back into the distillation zone.

7. The process according to claim 1, wherein a gas mixture containing solid by-products such as, for example, soot, is formed at a temperature of from 480 to 540° C. and a pressure of from 0.5 MPa and 3.0 MPa and may or may not be cooled to a temperature of from 180 to 280° C. in a heat recovery step, prior to further processing.

8. The process according to claim 1, wherein the gas mixture fed into the quench zone produces a bottom product that is recovered at the bottom of the quench zone, and further comprising the steps of:

maintaining the gas mixture in the quench zone at a lower pressure than the pressure prevailing in the stripping zone; and, adjusting the bottom product to a higher pressure than the pressure prevailing in the stripping zone by means of a pump.

9. The process according to claim 1, wherein the gas mixture originates from a 1,2-dichloroethane cracking process in which external 1,2-dichloroethane evaporation is used and a 1,2-dichloroethane elutriation stream is produced, the elutriation stream being used in the quench bottom product treatment, wherein said elutriation stream is either fed into the quench bottom product or, in the first step of the quench bottom product treatment, the external heat supply is replaced by a flash evaporator into which the quench bottom product and/or the elutriation stream are fed.

10. The process according to claim 1, wherein the cracking gas is formed from the non-catalytic pyrolysis of 1,2-dichloroethane to give vinyl chloride monomer, said process further comprising the steps of:

carrying out the thermal cracking of 1,2-dichloroethane at a temperature between 480 to 540° C., and at a pressure of from 0.5 MPa to 3 MPa;

cooling the reacted mixture to a temperature of from 180 to 280° C., optionally in a heat recovery step, followed by passing the cooled material into the quench zone wherein it is cooled and washed with the 1,2-dichloroethane-enriched condensate;

removing from 80 to 99% by weight, of the cooled cracking gases as quench gas in the form of vapors at the top of the quench zone;

removing from 1–20% by weight of the cooled cracking gases in liquid form as a first bottom discharge product from the quench zone;

passing the quench gas obtained from the top of the quench zone into the rectifying zone wherein the quench gas is separated into a distillate and a second bottom product;

discharging said second bottom product to yield the solids-free cracking gas condensate enriched in 1,2-dichloroethane;

separation of said second bottom product into first and second substreams;

feeding the first sub-stream to the stripping zone for further treatment;

feeding back the second sub-stream into the quench zone as a coolant and washing agent for treating the cracking gas, said second sub-stream comprising the 1,2-dichloroethane enriched solids-free cracking gas condensate;

feeding the distillate and the first sub-stream preliminary fraction separately for further distillative treatments; and feeding the first bottom product containing unwanted solid to another treatment step.

11. The process according to claim 10, wherein distillative treatment of the first sub-stream preliminary fraction takes place in the stripping zone, the 1,2-dichloroethane is recovered in enriched form with the bottom product formed therein, and the top product formed therein is fed back into the rectifying zone.

12. The process according to claim 1, further comprising the distillative separation of the solids-free gas mixture comprising vinyl chloride monomer, hydrogen chloride and unreacted 1,2-dichloroethane, wherein said gas mixture is formed from either catalytic or non-catalytic pyrolysis of 1,2-dichloroethane, said process further comprising the steps of:

maintaining the solids-free mixture at a temperature in the range from 85 to 540° C., and at a pressure of 0.1 MPa to 3.0 MPa;

feeding the solids-free mixture in gas from beneath the internals of a rectifying zone removing from the top of the rectifying zone, a rectified top product comprising hydrogen chloride, vinyl chloride monomer and other components having a lower boiling point than vinyl chloride monomer, and feeding the second mixture to a distillation zone;

separating the rectified top product in the distillation zone into a highly purified vinyl chloride monomer that is recovered as a bottom product in the distillation zone, and;

recovering at the top of the distillation zone, substantially pure hydrogen chloride along with other components of a lower boiling point than vinyl chloride monomer;

forming a rectified bottom product which is taken from the bottom of the rectifying zone and comprising 1,2-dichloroethane as a principal component, and including hydrogen chloride, vinyl chloride monomer and components that have a higher boiling point than vinyl chloride monomer;

feeding said rectified bottom product to a stripping zone either as a full stream, or as a sub-stream when an amount of said rectified bottom product is fed to the quench zone for use as quench liquid; and, separating said rectified bottom product in the stripping zone into a mixture of substantially pure 1,2-dichloroethane recovered at the bottom of the stripping zone with components having a higher boiling point than vinyl chloride monomer and negligible amounts of hydrogen chloride and vinyl chloride monomer and recovering at the top of the stripping zone, a top-recovered mixture of 1,2-dichloroethane and newly generated thermal break down products including hydrogen chloride and vinyl chloride monomer, and feeding said top-recovered mixture back into the rectifying zone for further treatment.

13. A process for the treatment of a cracking gas formed by pyrolysis of 1,2-dichloroethane, in which the cracking gas is split into its principal components hydrogen chloride, vinyl chloride and unreacted 1,2-dichloroethane, and these arise in substantially pure form, where, in the first step of the treatment of the cracking gas, the solids are separated off therefrom in a quenching zone, and the process is characterized in that:

in a rectifying zone following the quenching zone, all the hydrogen chloride and vinyl chloride is taken off as top product and fed to a distillation zone for separation, part of the bottom product from the rectifying zone is fed to a stripping zone, and the other part of the bottom product from the rectifying zone as 1,2-dichloroethane enriched, solids-free cracking gas condensate is employed as quenching liquid in the quenching zone through recycling, and that the top product from the stripping zone is fed back in its entirety into the rectifying zone.

* * * * *

UNITED STATES PATENT AND TRADEMARK OFFICE
CERTIFICATE OF CORRECTION

PATENT NO.   : 6,441,257 B1                                                               Page 1 of 1
DATED        : August 27, 2002
INVENTOR(S)  : Friedrich Seidelbach It is certified that error appears in the above-identified patent and that said Letters Patent is hereby corrected as shown below:

<u>Title page,</u>
Item [30], please add, Foreign Application Priority Data, to read as: April 7, 1998 (DE) 196 15 446.7. --
Item [63], add Related U.S. Application Data, to read as: -- Continuation of Application No. PCT/EP98/03680 filed on June 18, 1998. --

Signed and Sealed this

Twenty-sixth Day of November, 2002

Attest:

*Attesting Officer*

JAMES E. ROGAN
*Director of the United States Patent and Trademark Office*